United States Patent [19]

Goddard

[11] Patent Number: 4,683,004

[45] Date of Patent: Jul. 28, 1987

[54] FOAMABLE COMPOSITIONS AND PROCESSES FOR USE THEREOF

[75] Inventor: Errol D. Goddard, Haworth, N.J.

[73] Assignee: Union Carbide Corporation, Danbury, Conn.

[21] Appl. No.: 767,813

[22] Filed: Aug. 20, 1985

[51] Int. Cl.⁴ .......................... A61K 7/02; A61K 7/06; C08L 1/26

[52] U.S. Cl. ...................................... 106/170; 106/22; 252/DIG. 1; 252/DIG. 5; 252/DIG. 13; 424/DIG. 1; 424/40; 424/44; 424/47; 424/73

[58] Field of Search ..................... 536/90, 91; 106/122, 106/170; 252/DIG. 1, DIG. 13, DIG.5; 424/DIG. 1, 40, 44, 47, 73; 524/903

[56] References Cited

U.S. PATENT DOCUMENTS

| | | | |
|---|---|---|---|
| 3,177,119 | 4/1965 | Zoebelein | 524/903 |
| 3,518,343 | 6/1970 | Welsh et al. | 424/44 |
| 4,228,277 | 10/1980 | Landoll | 536/90 |
| 4,243,802 | 1/1981 | Landoll | 536/90 |
| 4,456,586 | 6/1984 | Vanlerberghe et al. | 424/DIG. 1 |
| 4,536,390 | 8/1985 | Padden | 424/DIG. 1 |

Primary Examiner—Ronald W. Griffin
Attorney, Agent, or Firm—Henry H. Gibson

[57] ABSTRACT

Foamable compositions comprising water, and a modified non-ionic cellulose ether prepared as described in U.S. Pat. No. 4,228,277 produce very stable foams. Accordingly, these compositions are suitable for use as foaming personal care products, such as hair styling mousses and foaming hand lotions and cleansers, and in other applications where stable foams are needed. In personal care products, foaming is desirably effected by an aerosol propellant included in the foamable composition.

38 Claims, No Drawings

FOAMABLE COMPOSITIONS AND PROCESSES FOR USE THEREOF

FIELD OF THE INVENTION

This invention relates to foamable compositions and processes for use thereof. More particularly, this invention relates to such foamable compositions and processes which contain certain non-ionic cellulose ethers as foam stabilizers.

It has long been known that various types of chemically modified polysaccharides, including some cellulose ethers, are useful as thickening and viscosifying agents in a variety of compositions, including paper-making compositions, personal care products, adhesives, printing inks, paints, etc. Some of the modified polysaccharides used as thickeners in personal care and other products are also known to possess significant surface activity i.e. the ability to lower the surface tension of water appreciably i.e. by 10 dyne/cm. or more.

There is, however, one type of personal care product in which the thickening and surface active properties of chemically modified polysaccharides would be useful, but for which most prior art chemically modified polysaccharides are not suitable. This type is the so-called "mousse products", a term which is used herein to mean a product which is originally prepared in an unfoamed state but which is allowed to foam before use so that the product is used for personal care in the foam state. Such mousse preparations include, for example, hair styling mousses, which are intended for application to wet hair after washing to facilitate the styling of the hair, and mousse products intended for use as hand care creams or hand washing agents.

Because such mousse compositions are used in a foamed form, it is essential that the foam produced by the mousse composition be stable for a period of at least several minutes. In addition, the foam must not break down as a result of, for example, manual manipulation of the hair during styling, in the case of hair styling mousse. Accordingly, personal care mousse compositions must contain a foam stabilizer capable of producing the necessary degree of stability in the foamed composition. Although most chemically modified polysaccharides have substantial thickening and viscosifying activity, they have limited foam stabilizing activity and hence are not suitable for use in personal care mousse compositions.

U.S. patent application Ser. No. 697,241, filed Feb. 1, 1985, unpublished at the date of filing of the present application but assigned to the same assignee as the present application, discloses hydrophobe substituted, water-soluble cationic polysaccharides which do have significant foam stabilizing properties sufficient to render them useful in personal care mousse compositions. However, hitherto no non-ionic substituted polysaccharide has been known to have sufficient foam stabilizing activity to render it suitable for use in personal care mousse compositions.

We have now discovered that a group of modified non-ionic cellulose ethers disclosed in U.S. Pat. No. 4,228,277 issued Oct. 14, 1980 to Landoll do possess sufficient foam stabilizing activity to render them useful in personal care mousse compositions, and in other compositions in which stable foams are required.

SUMMARY OF THE INVENTION

This invention provides a foamable composition comprising water, a non-ionic cellulose ether having a sufficient degree of non-ionic substitution selected from the class consisting of methyl, hydroxyethyl and hydroxypropyl to cause the ether to be water-soluble, the cellulose ether being further substituted with a long chain alkyl radical having 10 to 24 carbon atoms in an amount between about 0.2 weight percent and the amount which renders the cellulose ether less than 1% by weight soluble in water, and means for providing gas the composition for foam generation therein.

This invention also provides a process for preparing a stable, fine-celled foam, this process comprising procuring, in an unfoamed state, a composition comprising water and a non-ionic cellulose ether having a sufficient degree of non-ionic substitution selected from the class consisting of methyl, hydroxyethyl and hydroxypropyl to cause the ether to be water-soluble, the cellulose ether being further substituted with a long chain alkyl radical having 10 to 24 carbon atoms in an amount between about 0.2 weight percent and the amount which renders the cellulose ether less than 1% by weight soluble in water, and foaming this composition. This process may be used for personal care of the human body by applying the composition, before or after foaming, to the human body.

DETAILED DESCRIPTION OF THE INVENTION

As already mentioned, the non-ionic cellulose ethers used in the compositions and processes of the present invention are described and claimed in U.S. Pat. No. 4,228,277. Full details of the methods for preparing these non-ionic cellulose ethers are given in the aforementioned patent, and accordingly only a summary of the method of preparation is included here. A non-ionic cellulose ether to which the methyl, hydroxyethyl or hydroxypropyl substituents have been attached by conventional methods is slurried in an inert organic diluent such as a lower aliphatic alcohol, ketone or hydrocarbon and a solution of an alkali metal hydroxide is added to the resultant slurry at a low temperature. When the ether is thoroughly wetted and swollen by the alkali, a $C_{10}$ to $C_{24}$ epoxide is added and the reaction is continued, with agitation, until complete. Residual alkali is then neutralized and the product is recovered, washed with inert diluents, and dried. The etherification can also be effected with a $C_{10}$ to $C_{24}$ halide or halohydride, but these reagents are sometimes less reactive, less efficient and more corrosive than the epoxide, so that the latter is preferred. Substantially the same procedure can be used to attach the hydrocarbon modifier by an ester or urethane linkage In the non-ionic cellulose ethers the long chain alkyl radical is preferably attached by an ether linkage, and is preferably a hydroxypropyl or hydroxyethyl cellulose ether. A preferred group of non-ionic cellulose ethers are the hydroxyethyl ethers having a molecular weight, prior to substitution with the long chain alkyl group, of from about 20,000 to about 1,000,000, most desirably from about 50,000 to about 400,000.

The foamable composition of the present invention may be used in any application where stable foams are desired. Thus, in addition to their aforementioned use in personal care products, the compositions may be useful as fire-fighting or fire protective foams applied from foam-type fire extinguishers or foam guns to burning automobiles or aircraft, or on runways to help prevent fire during emergency landings. The compositions may also be useful in froth floatation process, for example in the separation of metalliferous ores from gangue, and in protective foams used to protect delicate agricultural crops against extreme cold.

The exact method used to effect foaming of the compositions of the present invention and in the processes of the present invention may vary depending upon a large number of factors including, for example, the type of other components (if any) present in the composition and the purpose for which the foam is being generated. Thus, the means for generating gas in the compositions of the present invention may comprise means for introducing gas under pressure (i.e. under a pressure greater than the pressure in the composition at the point where the gas enters the composition) into the composition. For example, when the compositions of the present invention are used in froth floation processes foaming may be effected by pumping air under pressure through air injection nozzles into the composition. The means for generating gas may also comprise two materials provided in the composition and capable of chemically reacting with one another to generate gas within the composition. For example, when the compositions of the present invention are used to generate fire fighting foams, they may contain a carbonate or bicarbonate and an acid capable of reacting with the carbonate or bicarbonate to generate carbon dioxide gas which foams the composition. Obviously, if foaming of the composition is not desired immediately after its preparation, the two gas-generating materials must be separated until foaming is desired, and those skilled in the art will be aware of various ways (e.g. the provision of frangible members or valves) by means of which such separation can be achieved. In the processes of the present invention, foaming of the composition may also be effected by mechanical agitation, for example by shaking a partially-empty container holding the composition or by vigorously stirring the composition.

Whatever method is used for foaming the composition, the relative proportions of water and non-ionic cellulose ether in the composition should be chosen so that a stable foam is produced. Typically the compositions may comprise from about 0.1 to about 10 percent by weight of the non-ionic cellulose ether and from about 99.9 to about 90 percent by weight of water, based upon the total weight of the non-ionic cellulose ether and water.

Especially when the compositions of the present inventions are intended for use in personal care products, the preferred means for providing gas in the composition is the inclusion of an aerosol propellant in the composition. (The term "aerosol propellant" is used herein in its conventional meaning in the art, namely to denote a compound which has, at room temperature, a vapor pressure greater than one atmosphere but sufficiently low that it can be stored safely at room temperature in the liquid state under the pressures of a few atmospheres used in the conventional aerosol containers, the propellant being sufficiently volatile that upon release of pressure it will rapidly vaporize at room temperature and leave the container in which it is placed.)

The relative proportions of the water, propellant and non-ionic cellulose ether in such propellant-containing compositions of the present invention must be chosen so that the composition is foamable i.e. so that upon release of pressure from the composition, and consequent volatilization of the propellant, the composition is transformed into a foam rather than an aerosol. As is well known to those skilled in the art, the proportion of propellant used in such foamable compositions is generally lower than that used in aerosol compositions. Provided the composition is foamable, the relative proportions of the components may vary widely. For example, the propellant-containing foamable compositions of the present invention may comprise from about 0.1 to about 5% by weight of the non-ionic cellulose ether, from about 45 to about 95% by weight of water and from about 5 to about 50% by weight of the propellant, preferred compositions being those containing from about 0.3 to about 2% by weight of the non-ionic cellulose ether, from about 70 to about 90% weight by of water and from about 30 to about 10% by weight of the propellant, the percentages in all cases being based upon the total weight of the non-ionic cellulose ether, water and propellant in the composition.

The propellant used in the foamable compositions of the present invention may be any of the propellants known in the art, subject to the proviso that, if the compositions are intended for application to the human body, propellants which are toxic or irritating to any part of the human body, for example the skin, eyes, or lungs should be avoided. It is preferred that the propellant be a hydrocarbon propellant, since such propellants are inexpensive, readily available and pose no significant risk of toxicity or irritation to the user. More specifically, preferred propellants include propane, isobutane and mixtures thereof.

The rate at which propellant-containing compositions of the present invention foam will vary with a number of factors, including the exact amount and chemical composition of the non-ionic cellulose ether, of the propellant and of the other components of the composition. Some of the compositions of the invention will foam almost instantly upon release of pressure from the composition, while others may be of the so-called "delayed foaming" type, which emerge from the aerosol container in an unfoamed state, only achieving their final foamed form after a significant delay, typically 3-60 seconds. Such delayed foaming compositions are useful as, for example, foaming shaving creams which are applied to the face in liquid form and foam on the face, or as foaming hand creams. Since the propellant-containing compositions of the present invention may be of the rapid foaming or of the delayed foaming type, in the process of the present invention for personal care, application of the composition to the human body may occur either before or after foaming of the composition.

The foamable compositions of the present invention need only contain water, the non-ionic cellulose ether and the propellant, and indeed in certain applications no other components may be necessary or desirable. For example, since the non-ionic cellulose ethers possess substantial thickening and surface active properties as well as their foam stabilizing properties, a satisfactory hair styling mousse composition can be prepared by using only water, the propellant and the non-ionic cellulose ether. This is in contrast to hair styling mousses made with prior art chemically modified polysaccharides in which, because of the limited surface activity of the polysaccharides, it has normally been necessary, in practice, to include a surfactant in addition to the polysaccharide. However, the compositions of the present invention may include other additives previously used in compositions of similar types. For example, compositions of the present invention intended for use as hair styling mousses, foaming hand or body cleansers or shaving foams, may contain, in addition to the surface-active non-ionic cellulose ether, other surfactants such as, for example, triethanolamine lauryl sulfate, lauric diethanolamide, sodium lauryl sulfate and alkyl ethoxysulfates, and soaps etc. Non-ionic and cationic surfactants may also be included. Compositions of the present invention intended for use as hand and skin lotions may contain an oil, such as a mineral oil, emulsified in the water of the foamable composition and/or a water-soluble moisturizer, for example, glycerol, hyaluronic acid, propylene glycol or pyrrolidone carboxylate. The compositions of the present invention intended for use as personal care products may also contain a non-toxic water-miscible alcohol, such as ethanol or isopropanol. The inclusion of such an alcohol may be desirable either for esthetic reasons (i.e. the pleasant sensation the alcohol generates as it evaporates from the skin of the user) or because the alcohol acts as a co-solvent for other ingredients, for example perfumes and coloring agents, which are not very water-soluble.

These additives may be used in personal care compositions of the present invention in substantially the same proportions as that in which they have been used in prior art personal care products of similar types allowing if necessary for the fact that the compositions of the present invention may contain a propellant which volatilizes during use, so that the amounts of the additives present should be chosen relative based upon the amount of water present in the compositions of the present invention. For example, when a surfactant is added to the compositions it may be added in amount of about 0.001% up to about 10% by weight of the water in the composition, although because of the high surface activity of the non-ionic cellulose ethers used in the present invention, the amount of surfactant normally need not be as great as in prior art compositions. When an emulsified mineral oil is present in the water of the foamable composition, it may be present in an amount of about 40 parts of mineral oil per 60 parts of water. Such oil-in-water emulsions can be readily be prepared by conventional methods known to those skilled in the art, for example heating the two phases separately to around 70° C. and then mixing them with vigorous agitation. As regards the aforementioned moisturizers, glycerol may be added in an amount up to about 20% by weight of the water in the composition, hyaluronic acid in an amount up to about 0.05% by weight of the water and pyrrolidone carboxylate in an amount up to about 1% by weight of the water. Alcohols such as ethanol and isopropanol may comprise up to about 30% by weight of the composition.

The aforementioned types of additives are mentioned by way of example only and further types of additives may be included in the compositions of the present invention, as will be apparent to those skilled in the art, the types of additives varying of course with the intended use of the composition. For example, it may be desirable to include in the compositions of the present invention stabilizers such as methylparaben and propylparaben. The following Examples are now given, though by way of illustration only, to illustrate the foam stabilizing properties of the non-ionic cellulose ethers used in the compositions at the processes of the present invention, and to illustrate a composition of the present invention usable as a hair styling mousse. In the following Examples, a non-ionic cellulose ether used in the compositions of the present invention is compared with various prior art chemically modified polysaccharides. It should be noted that the chemically modified polysaccharide used in the following Examples produced in accordance with the aforementioned U.S. patent application Ser. No. 697,241 is not a typical chemically modified polysaccharide, but rather a chemically modified polysaccharide having truly outstanding foam stabilization properties which, so far as we are aware, are greatly superior to the foam stabilization properties of all chemically modified polysaccharides disclosed in the prior art.

EXAMPLE 1

This Example illustrates the foam stabilization properties of the non-ionic cellulose ethers used in the compositions of the present invention, as compared with various chemically modified polysaccharides. All viscosities quoted are at approximately ambient temperature (about 25° C.).

The following materials were used in foam stabilization tests:

HM-HEC WSPD-330 (hereinafter abbreviated HMHEC): a modified non-ionic cellulose ether useful in the compositions and processes of the present invention. This material is sold commercially by Hercules Incorporated, Wilmington, DE and is produced in accordance with the aforementioned U.S. Pat. No. 4,228,277. A 1% by weight aqueous solution of this cellulose ether has a viscosity of approximately 400cP.

HMQNHEC: a hydrophobe modified quaternary nitrogen hydroxethyl cellulose, a water-soluble cationic polysaccharide manufactured by Union Carbide Corporation, Danbury, CT 06817, in accordance with the aforementioned copending U.S. patent application Ser. No. 697,241. A 1% by weight aqueous solution of this material has a viscosity of approximately 200 cP.

Polymer JR 125: a cationic polysaccharide manufactured by Union Carbide Corporation; a 2% by weight aqueous solution of this material has a viscosity of approximately 125 cP.

CELLOSIZE PCG-10: a hydroxyethyl cellulose manufactured by Union Carbide corporation; a 1% by weight aqueous solution of this material has a viscosity of approximately 5000 cP.

Methocel(A-4M): a methylated cellulose manufactured by Dow Chemical Company, Midland, MI; a 2% by weight aqueous solution of this material has a viscosity of approximatly 4000 cP.

Methocel(A-4C): a methylated cellulose manufactured by Dow Chemical Corporation; a 2% by weight aqueous solution of this material has a viscosity of approximately 400 cP.

Sodium dodecyl sulfate (abbreviated "SDS")

0.1 percent aqueous solutions of all the test materials were prepared. 30 ml. of each aqueous solution were placed in a separate 100 ml. volumetric cylinder, which was then capped. The cylinder was shaken vigorously by hand for 30 seconds and the height of the resulting foam read (on the volume scale of the cylinder) as a function of time for a period of 20 hours. The results are shown in Table 1 below.

TABLE 1

| | Foam Height (mm) | | | | |
|---|---|---|---|---|---|
| | Initial | 10 min. | 1 hour | 3 hours | 20 hours |
| HMHEC | 22 | 22 | 20 | 20 | 8 |
| HMQNHEC | 30 | 30 | 26 | 22 | 7 |
| Polymer JR 125 | 15 | 2 | 0 | 0 | 0 |
| HEC (PCG-10) | 16 | 10 | 3 | 2 | 0 |
| Methocel (A-4M) | 25 | 12 | 4 | 2 | 0 |
| Methocel (A-4C) | 25 | 15 | 5 | 5 | 0 |
| SDS | 70+ | 70+ | 19 | 19 | 6 |

From the data in Table 1 it will be seen that the foam stabilizing activity of the HMHEC was approximately the same as that of the HMQNHEC and greatly superior to that of the other polymers tested. This superiority is reflected both in the height of the foam generated initially and its short term stability (up to one hour), but more especially in its long term stability, as measured by the foam height at three hours and beyond. Thus, in this test the non-ionic cellulose ether useable in the compositions and processes of the present invention produced results as good as the cationic HMQNHEC which, as already mentioned, possesses extraordinary foam stabilizing ability.

Although the sodium dodecyl sulfate (which is a non-polymeric surfactant with little viscosifying and thickening ability) produces a great deal of foam, the quality of this foam is very different from that of the foams produced by the polymers. Liquid drains from the sodium dodecyl sulfate much more quickly than from the foams produced by the polymers and the rate of decay of the SDS foam is relatively much higher; for example, after three hours only a thin skeleton of the original SDS foam remains. Slow drainage of liquid from a foam is essential in a mousse composition, which thus requires a material possessing substantial foam stabilization and thickening properties, as well as surface activity.

EXAMPLE 2

This Example illustrates a composition of the present invention useable as a hair styling mousse and similar compositions using prior art chemically polysaccharides.

The materials used in these tests were the HMHEC, HMQNHEC, Methocel (A-4C), and CELLOSIZE HEC (PCG-10) described in Example 1 above, and Polymer JR 400 (polyquaternium 10, a cationic polysaccharide, manufactured by Union Carbide Corporation; a 2% by weight aqueous solution of this material has a viscosity of approximately 400 cP). One percent by weight aqueous solutions of all these polymers were prepared and charged to aluminum mousse containers together with an isobutane/propane propellant, the charging ratio being 80% by weight of the aqueous solution to 20% by weight of the propellant.

A small quantity of each composition was dispensed, in foamed form, from the mousse containers and the appearance of the foam observed for a period of 10 minutes. The results obtained are shown in Table 2 below.

TABLE 2

| | 10 secs. | 1 min. | 10 min. |
|---|---|---|---|
| HMHEC | Very good Stable, dry | Very good Stable, dry | Very good Stable, dry |
| HMQNHEC | Very good Stable, dry | Very good Stable, dry | Very good Stable, dry |
| Methocel (A-4C) | Poor, flat and Very wet | Poor, flat wet | |
| HEC (PCG-10) | Good | Good Flattening | Fairly Good Flat |
| Polymer JR 400 | Good | Fair Collapsing | |

From the data presented in Table 2 above, it will be seen that HMHEC foam displayed excellent stability and a stable dry nature substantially the same as the outstanding properties of the HMQNHEC foam, and greatly superior to these same properties of the other three polymers. It was apparent by visual observation that the foams produced by the HMHEC and HMQNHEC polymers were drier and had significantly finer and more stable cells than those produced by the other three polymers.

It will be apparent to those skilled in the art that numerous changes and modifications can be made in the preferred embodiments in the invention described above without departing from the scope of the invention. Accordingly, the whole of the foregoing description is to be construed in an illustrative and not in a limitative sense, the scope of the invention being defined solely by the appended claims.

What is claimed is:

1. A foamable composition comprising water; foam stabilizer consisting essentially of a non-ionic cellulose ether having a sufficient degree of non-ionic substitution selected from the class consisting of methyl, hydroxyethyl and hydroxypropyl to cause the ether to be water-soluble, the cellulose ether being further substituted with a long chain alkyl radical having 10 to 24 carbon atoms in an amount between about 0.2 weight percent and the amount which renders the cellulose ether less than 1% by weight soluble in water; and means for providing gas in the composition for foam generation therein.

2. A foamable composition according to claim 1 wherein, in the non-ionic cellulose ether, the long chain alkyl radical is attached via an ether linkage.

3. A foamable composition according to claim 1 wherein the non-ionic cellulose ether is a hydroxypropyl or hydroxyethyl cellulose ether.

4. A foamable composition according to claim 3 wherein the non-ionic cellulose ether is a hydroxyethyl cellulose ether having a molecular weight, prior to substitution with the long chain alkyl group, of from about 20,000 to about 1,000,000.

5. A foamable composition according to claim 4 wherein the non-ionic cellulose ether has a molecular weight, prior to substitution with the long chain alkyl group, of from about 50,000 to about 400,000.

6. A foamable composition according to claim 1 wherein the gas provision means comprises means for introducing gas under pressure into the composition.

7. A foamable composition according to claim 1 wherein the gas provision means comprises two materials capable of chemically reacting with one another and thereby generating gas within the composition.

8. A foamable composition according to claim 1 wherein the gas provision means comprises an aerosol propellant.

9. A foamable composition according to claim 8 comprising from about 0.1 to about 5 percent by weight of the non-ionic cellulose ether, from about 45 to about 95 percent by weight of water and from about 5 to about 50 percent by weight of the propellant, based upon the total weight of the non-ionic cellulose ether, water and propellant.

10. A foamable composition according to claim 9 comprising from about 0.3 to about 2 percent by weight of the non-ionic cellulose ether, from about 70 to about 90 percent by weight of water and from about 30 to about 10 percent by weight of the propellant, based upon the total weight of the non-ionic cellulose ether, water and propellant.

11. A foamable composition according to claim 8 wherein the propellant is a hydrocarbon propellant.

12. A foamable composition according to claim 11 wherein the propellant comprises propane, isobutane or a mixture thereof.

13. A foamable composition according to claim 1 further comprising any one or more of a surfactant, an oil emulsified in the water of the foamable composition, a water-miscible alcohol and a water-soluble moisturizer.

14. A foam produced by foaming of a composition according to claim 1.

15. A foam having a liquid phase comprising water and foam stabilizer which is a non-ionic cellulose ether having a sufficient degree of non-ionic substitution selected from the class consisting of methyl, hydroxyethyl and hydroxypropyl to cause the ether to be water-soluble, the cellulose ether being further substituted with a long chain alkyl radical having 10 to 24 carbon atoms in an amount between about 0.2 weight percent and the amount which renders the cellulose ether less than 1% by weight soluble in water.

16. A foam according to claim 15 wherein the liquid phase comprises from about 0.1 to about 10 percent by weight of the non-ionic cellulose ether and from about 99.9 to about 90 percent by weight of water, based upon the total weight of the non-ionic cellulose ether and water.

17. A process for effecting personal care of the surface of the human body, which process comprises:
procuring, in an unfoamed state, a composition comprising water, and foam stabilizer which is a non-ionic cellulose ether having a sufficient degree of non-ionic substitution selected from the class consisting of methyl, hydroxyethyl and hydroxypropyl to cause the ether to be water-soluble, the cellulose ether being further substituted with a long chain alkyl radical having 10 to 24 carbon atoms in an amount between about 0.2 weight percent and the amount which renders the cellulose ether less than 1% by weight soluble in water;
foaming the composition; and
applying the foamed or unfoamed composition to the human body.

18. A process according to claim 17 wherein, in the non-ionic cellulose ether, the long chain alkyl radical is attached via an ether linkage.

19. A process according to claim 17 wherein the non-ionic cellulose ether is a hydroxypropyl or hydroxyethyl cellulose ether.

20. A process according to claim 19 wherein the non-ionic cellulose ether is a hydroxyethyl cellulose ether having a molecular weight, prior to substitution with the long chain alkyl group, of from about 20,000 to about 1,000,000.

21. A process according to claim 20 wherein the non-ionic cellulose ether has a molecular weight, prior to substitution with the long chain alkyl group, of from about 50,000 to aout 400,000.

22. A process according to claim 17 wherein the foaming of the composition is effected by mechanical agitation.

23. A process according to claim 17 wherein the foaming of the composition is effected by introducing gas under pressure into the composition.

24. A process according to claim 17 wherein the foaming of the composition is effected by chemical reaction between two components of the composition, this chemical reaction generating gas within the composition.

25. A process according to claim 17 wherein the foaming of the composition is effected by volatilization of an aerosol propellant in the composition.

26. A process according to claim 25 wherein the unfoamed composition comprises from about 0.1 to about 5 percent by weight of the non-ionic cellulose ether, from about 45 to about 95 percent by weight of water and from about 5 to about 50 percent by weight of the propellant, based upon the total weight of the non-ionic cellulose ether, water and propellant.

27. A process according to claim 26 wherein the unfoamed composition comprises from about 0.3 to about 2 percent by weight of the non-ionic cellulose ether, from about 70 to about 90 percent by weight of water and from about 30 to about 10 percent by weight of the propellant, based upon the total weight of the non-ionic cellulose ether, water and propellant.

28. A process according to claim 25 wherein the propellant is a hydrocarbon propellant.

29. A process according to claim 28 wherein the propellant comprises propane, isobutane or a mixture thereof.

30. A process according to claim 17 wherein the foamable composition further comprises a surfactant and the foam is applied to the hair or skin.

31. A process according to claim 17 wherein the foamable composition further comprises an oil emulsified in the water and the foam is applied to the skin.

32. A process according to claim 17 wherein the foamable composition further comprises a water-soluble moisturizer and the foam is applied to the skin.

33. A process for preparing a stable, fine-celled foam, which process comprises:
procuring, in an unfoamed state, a composition comprising water and foam stabilizer which is a non-ionic cellulose ether having a sufficient degree of non-ionic substitution selected from the class consisting of methyl, hydroxyethyl and hyroxypropyl to cause the ether to be water-soluble, the cellulose ether being further substituted with a long chain alkyl radical having 10 to 24 carbon atoms in an amount between about 0.2 weight percent and the amount which renders the cellulose ether less than 1% by weight soluble in water; and
foaming the composition 34. A process according to claim 33 wherein the non-ionic cellulose ether is a hydroxyethyl cellulose ether having a molecular weight, prior to substitution with the long chain alkyl group, of from about 20,000 to about 1,000,000.

35. A process according to claim 33 wherein the foaming of the composition is effected by mechanical agitation.

36. A process according to claim 33 wherein the foaming of the composition is effected by introducing gas under pressure into the composition.

37. A process according to claim 33 wherein the foaming of the composition is effected by chemical reaction between two components of the composition, this chemical reaction generating gas within the composition.

38. A process according to claim 33 wherein the foaming of the composition is effected by volatilization of an aerosol propellant in the composition.

* * * * *